United States Patent [19]
Kennedy et al.

[11] Patent Number: 6,017,921
[45] Date of Patent: *Jan. 25, 2000

[54] CRYSTALLINE TRIMETREXATE SALTS AND THE PROCESS FOR MAKING THE SAME

[75] Inventors: Paul Kennedy, Phoenixville, Pa.; Ingomar Grafe, Nürnberg, Germany; Johann Peter Mörsdorf, Langenzenn, Germany; Kurt-Henning Ahrens, Nürnberg, Germany

[73] Assignee: U.S. Bioscience, Inc., West Conshohocken, Pa.

[ * ] Notice: This patent is subject to a terminal disclaimer.

[21] Appl. No.: 09/018,515

[22] Filed: Feb. 4, 1998

Related U.S. Application Data

[63] Continuation of application No. 08/372,254, Jan. 13, 1995, Pat. No. 5,716,960.

[51] Int. Cl.[7] .................... A61K 31/505; C07D 239/95
[52] U.S. Cl. ............................. 514/260; 544/291
[58] Field of Search .............................. 514/260; 544/291

[56] References Cited

U.S. PATENT DOCUMENTS

| | | | |
|---|---|---|---|
| 4,376,858 | 3/1983 | Colbry | 544/291 |
| 4,853,221 | 8/1989 | Elslager et al. | 424/649 |
| 5,716,960 | 2/1998 | Kennedy | 544/291 |

FOREIGN PATENT DOCUMENTS

| | | |
|---|---|---|
| 0 051 415 | 5/1982 | European Pat. Off. . |
| 1 345 502 | 1/1974 | United Kingdom . |

OTHER PUBLICATIONS

Robinson, C., 1994, "Trimetrexate glucuronate", Drugs of Today 30(5):347–355.

Hempel, A. et al., 1988, "Trimetrexate: Molecular structures and conformational similarities in two crystal forms", Cancer Biochem. Biophys. 10(1):25–30 .

Sutton, P.A. & Cody, V., 1987, "Conformational Analysis of Antineoplastic Antifolates: The Crystal Structure of Trimetrexate and the Aminopterine Derivative 4–[N–[2, 4–Diamino–6–pteridinyl)methyl]amino]benzoic Acid", J. Med. Chem. 30:1843–1848.

Cell cycle effects of trimextrexate (CI–898), *Cancer Chemotherapy and Pharmacology*, Hook et al., vol. 16, No. 2, 1986, pp. 116–120 (1985).

*Primary Examiner*—Richard L. Raymond
*Attorney, Agent, or Firm*—Pennie & Edmonds, LLP

[57] ABSTRACT

The present invention provides for a crystalline form of trimetrexate either as a glucuronate, acetate, hydrochloride, methanosulfonate or lactate salt, which can be processed galenically as a stable, well-defined solid substance and processes for producing the crystalline forms. Such crystalline forms allow for prolonged stability in storage and for oral and intravenous administration of the drug.

9 Claims, 11 Drawing Sheets

CRYSTALLINE TRIMETREXATE SALTS AND THE PROCESS FOR MAKING THE SAME

This is a continuation of application Ser. No. 08/372,254, filed Jan. 13, 1995, now U.S. Pat. No. 5,716,960.

1. FIELD OF THE INVENTION

The present invention is directed to novel crystalline forms of trimetrexate salts and the novel processes four making crystalline trimetrexate salts.

2. BACKGROUND OF THE INVENTION

The 2,4-diamino-5-methyl-6-[(3,4,5-trimethoxyanilino) methyl] quinazoline salts ("trimetrexatel") are known to have antineoplastic, antiparasitic and antibacterial activity. Trimetrexate is a potent inhibitor of the enzyme dihydrofolate reductase ("DHFR") that is known to catalyze the synthesis of nucleotide precursors of DNA and RNA. Inhibition of this enzyme results in cellular depletion of reduced folates, which are necessary for various cellular process, including RNA and DNA synthesis, and ultimately results in cell death. It is this property that gives trimetrexate its antineoplastic, antiparasitic and antibacterial activity.

Trimetrexate has demonstrated antitumor activity against a range of experimental murine and human tumor cell lines, in vitro and in vivo. For example, trimetrexate has shown antitumor activity against murine cell lines such as L1210, L5178Y, S-180, W-256 in vitro. In addition, trimetrexate has shown antitumor activity against human tumor cells lines derived from breast, colon, lung, ovary, renal cell and melanoma cells in vitro. In vivo studies have demonstrated that trimetrexate has therapeutic utility against murine tumors such as B16 melanoma, colon 26 and 38, L1210 and p388 leukemia and CD8F mammary tumors. Other possible uses for trimetrexate include the treatment of malaria, psoriasis, rheumatoid arthritis and prophylaxis against Pneumocystis carinii pneumonia.

Trimetrexate as the free base is a lipophilic DHFR with very low water solubility. To increase the aqueous solubility the Warner-Lambert Company synthesized a number of various salts which were disclosed by Colbry in U.S. Pat. No. 4,376,858 and issued on Mar. 15, 1983 and assigned to the Warner-Lambert Company. The preferred salt reported by Colbry was trimetrexate glucuronate due to its superior water solubility, stability and low toxicity of glucuronic acid. The method disclosed by Colbry gives a method of preparation where trimetrexate and glucuronic acid are dissolved in warm methanol and ethyl acetate and followed by cooling to precipitate the salt. The Colbry patent states that the disclosed trimetrexate glucuronate salt is non-crystalline.

J. L. Hicks et al., J. Labelled Compound Radiopharm. 29, 415 (1991) disclose another method of manufacture of trimetrexate glucuronate salt. In this method trimetrexate free base and glucuronic acid are added to an aqueous solution in an ampoule, followed by lyophilization to form a solid. This method also produces an amorphous salt.

An injectable form of amorphous trimetrexate glucuronate has received marketing authorization in the United States and Canada under the trade name Neutrexin by U.S. Bioscience (West Conshohocken, Pa.) for use in combination with leucovorin for the treatment of moderate to severe Pneumocystis carinii pneumonia in immunocompromised patients, e.g., those suffering from AIDS (U.S. Bioscience's Neutrexin for PCP, Scripp 1886/87, 31(1994).

A. Hempel et al., Cancer Biochem. Biophys. 10, 25–30 (1988), discloses the crystal structures of trimetrexate acetate monohydrate and hydrated trimetrexate free base. There is no suggestion regarding crystalline trimetrexate glucurotiate or the method of making the same.

H. K. Chan et al., J. Crystal Growth 94, 488–498 (1989) discloses techniques for modifying the crystallization of methotrexate. The presence of trimetrexate in solution was shown to affect the crystalline habit of the methotrexate that is precipitated. There is no suggestion regarding the crystallization of trimetrexate glucuronate.

P. L. Stetson et al., J. Chromatography 464, 163–71 (1989) discusses the stability of the trimetrexate glucuronate salt: obtained from Warner Lambert/Parke-Davis, Pharmaceutical Research Division. This salt is apparently that obtained by the process disclosed in the U.S. Pat. No. 4,376,858, which is assigned to Warner Lambert. It indicates that the salt has a half-life in solution of $51.6 \pm 0.8$ days at 37° C.

It is recognized that the amorphous form of trimetrexate salts is not the preferred form as a drug substance for oral administration. Accordingly, there is a strong need in the art for suitable methods for producing quantities of highly purified, medical grade trimetrexate salts having a crystalline structure, in order to obtain high and uniform stability during storage, and to provide oral forms of trimetrexate medications with good stability and bioavailability.

3. SUMMARY OF THE INVENTION

The present invention provides for crystalline forms of trimetrexate, either as a glucuronate, acetate, hydrochloride, methanesulfonate or lactate salt, which can be processed galenically as stable, well-defined solid substances. Such crystalline forms allow for prolonged stability in storage and for oral and intravenous administration of the drug.

Trimetrexate base is treated with a soft carbon acid, i.e, gluconic acid, glucuronic acid, lactic acid, acetic acid etc., but preferably gluconic acid, in either an aqueous or hydroalcoholic solution to solubilize the free base. The trimetrexate solution is heated to between 40 to 80° C. and stirred until practically homogeneous, treated with charcoal and vacuum filtered. The filtrate is treated with an excess of either the desired acid or conjugate base of the acid to give the desired trimetrexate salt. The solution is cooled to 20° C., filtered and the crystals washed with an appropriate solvent followed by drying under vacuum.

The present invention further provides for novel processes for producing crystalline trimetrexate salts of good quality. In one preferred embodiment, the present invention provides for a novel process for producing crystalline trimetrexate glucuronate salt of good quality.

The process is characterized as follows:
a. water is used as a solvent;
b. excess glucuronic acid is used to prevent the co-precipitation of the trimetrexate free base with the desired trimetrexate glucuronate salt;
c. n-heptane is used in the water solution as an antifoaming agent;
d. the crystalline trimetrexate glucuronate salt is filtered and washed with a 2% glucuronic acid solution;
e. the salt is dried at an elevated temperature in the range of 40 to 50 degrees under vacuum so as to avoid decomposition of the salt, and the formation of lumps and agglomerates.

In another preferred embodiment, the present invention provides for a novel process for producing crystalline trimetrexate acetate hydrate salt of good quality. The process is characterized as follows:

a. ethanol, 20 to 30 percent in aqueous medium is used as a solvent to dissolve trimetrexate free base;

b. excess gluconic acid is then added to form trimetrexate gluconate and to prevent the co-precipitation of the trimetrexate free base with the resulting trimetrexate gluconate salt;

c. excess acetic acid is then added to convert the trimetrexate gluconate to the acetate salt;

d. the crystalline trimetrexate acetate hydrate is filtered and washed with a 3 to 7 percent acetic acid solution;

e. the salt is dried at an elevated temperature in the range of 70 to 80 degrees under vacuum so as to avoid decomposition of the salt, and to avoid the formation of lumps and agglomerates.

In a further preferred embodiment, the present invention provides for a novel process for producing crystalline trimetrexate hydrochloride hydrate salt of good quality. The process is characterized as follows:

a. water is used as a solvent to dissolve the trimetrexate free base;

b. excess gluconic acid is then added to form trimetrexate gluconate and to prevent the co-precipitation of the trimetrexate free base with the resulting trimetrexate gluconate salt;

c. excess sodium chloride is then added to convert the trimetrexate gluconate to the hydrochloride salt;

d. the crystalline trimetrexate hydrochloride hydrate is filtered and washed with an aqueous ethanol solution of 75 to 85 percent;

e. the salt is dried at an elevated temperature in the range of 70 to 80 degrees under vacuum so as to avoid decomposition of the salt, and the formation of lumps and agglomerates.

In a further preferred embodiment, the present invention provides for a novel process for producing crystalline trimetrexate methanesulfonate salt of good quality. The process is characterized as follows:

a. water is used as a solvent to dissolve the trimetrexate free base;

b. excess gluconic acid is then added to form trimetrexate gluconate and to prevent the co-precipitation-of the trimetrexate free base with the resulting trimetrexate gluconate salt;

c. excess methanesulfonic acid is then added to convert the trimetrexate gluconate to the methanesulfonate salt;

d. the crystalline trimetrexate methanesulfonate is filtered and washed with a water solution;

e. the salt is dried at an elevated temperature in the range of 75 to 90 degrees under vacuum so as to avoid decomposition of the salt, and the formation of lumps and agglomerates.

In yet a further preferred embodiment, the present invention provides for a novel process for producing crystalline trimetrexate lactate hydrate salt of good quality. The process is characterized as follows:

a. water is used as a solvent to dissolve the trimetrexate free base;

b. excess L-(+)-lactic acid is then added to convert the trimetrexate base to the lactate salt;

c. the crystalline trimetrexate lactate hydrate is filtered and washed with a 50% aqueous ethanol solution to avoid yield losses due to the dissolution of the salt;

d. the salt is dried at an elevated temperature in the range of 70 to 80 degrees under vacuum so as to avoid decomposition of the salt, and the formation of lumps and agglomerates.

4. BRIEF DESCRIPTION OF THE DRAWINGS

Table 1 indicates the peak positions and intensities of the x-ray powder diffraction pattern of crystalline trimetrexate glucuronate hydrate salt.

Table 2 indicates the peak positions and intensities of crystalline trimetrexate acetate hydrate salt.

Table 3 indicates the peak positions and intensities of crystalline trimetrexate hydrochloride hydrate salt.

Table 4 indicates the peak positions and intensities of crystalline trimetrexate methanesulfonate salt.

Table 5 indicates the peak positions and intensities of crystalline trimetrexate lactate hydrate salt.

5. DESCRIPTION OF THE PREFERRED EMBODIMENTS

It has been discovered that contamination and decreased yield of the trimetrexate salts can be avoided in part by careful control of the purity of the reagents used in the crystallization of the salt.

The purity of the glucuronic acid used in the preparation of the glucuronate and other crystalline salts should be high. Glucuronic acid is obtained either synthetically from glucose via a several step process or from natural products-of flora, such as cherry gum (see, C. L. Mehltretter, et al. *J. Amer. Chem. Soc.* 73, 2424 (1951)). When synthetically prepared, the glucuronic acid may be contaminated by oxalate ions, calcium cations and reaction by-products. These contaminants should be removed by ion exchange or other suitable methods prior to use in the present crystallization process.

Likewise, the purity of the trimetrexate free base should be high. Possible contaminants of the trimetrexate free base include: 3, 4, 5-trimethoxyaniline, 2,4-diamino-5-methyl-6-quinazoline carboxaldehyde, 6-aminomethyl-5-methyl-2,4-quinazoline diamine, 2-amino-4-hydroxy-5-methyl-6-[(3,4,5-trimethoxyanilino)methyl] quinazoline and 2,4-diamino-5-methyl-6-quinazoline hydroxymethyl.

The general process for producing crystalline trimetrexate glucuronate hydrate is as follows:
a. mix trimetrexate free base and glucuronic acid or a precursor of glucuronic acid in water at about 60–70° C. until a homogeneous solution is formed;
b. filter the homogeneous solution through a clarifying filter;
c. cool the filtered solution down to about 40° to about 50° C.;
d. add an anti-foaming agent such as heptane to the solution;
e. cool the solution to about 20° C. over 1 hour, then cool to 10° C. for 1 hour and then to 5° C., filter off trimetrexate glucuronate crystals and wash the crystals with about a 2% trimetrexate glucuronate solution to form a slurry; and
f. stir the trimetrexate glucuronate slurry in acetone, filter and dry the crystals at about 50° C. in vacuum.

A precursor of glucuronic acid useful in the above process is glucuronic acid-lactone, which can be hydrolyzed into glucuronic acid by reaction with water.

The preferred molar ratio of trimetrexate free base to the glucuronic acid or its precursor is from about 1.17 to about 1.22. An excess of the glucuronic acid is required to prevent the precipitation of the trimetrexate free base and ensure the complete conversion of this base to the salt. Too great an excess of the glucuronic acid, however, may cause the co-precipitation of the glucuronic acid. Further, a molar ratio of trimetrexate free base to the glucuronic acid of less than 1.17 results in greater difficulty in completely dissolving the trimetrexate free base in the water within a short period of time.

The amount of water used in dissolving the trimetrexate free base and the glucuronic acid is determined by the solubility of the reagents as well as the stirability of the solution. Preferably, the amount of water is about 500 ml of water per kilogram of the trimetrexate free base.

Preferably, n-heptane, octanol or toluene can be added to the aqueous solution to reduce foaming.

The solution is clarified by a clarifying medium selected from the group consisting of bentonite, montmorillonite or other acid washed bleaching earths or synthetic silica in order to remove colored impurities such as polar oxidation products.

Once the crystalline trimetrexate glucuronate hydrate salt is formed in the cooled solution, the salt is filtered to separate it from the solution. The filtered salt is washed with about 2% glucuronic acid solution to remove colored impurities and avoid dissolving the salt. The salt, is then dried by slurrying in anhydrous acetone which should not contain more than 1% water, filtering and drying the salt in vacuum at about 50° C. to a water content of about 3% to about 9% to thereby form the mono-, di- or trihydrate form of trimetrexate glucuronate hydrate salt. The temperature and length of time for drying are chosen so as to avoid decomposing the salt and to efficiently attain the correct water content.

Decomposition products present with the salt may be qualitatively analyzed by HPLC, thin layer chromatography or NMR analysis.

For the preparation of the acetate, hydrochloride and methanesulfonate salts of trimetrexate, it is preferred to first convert trimetrexate base to the gluconate salt by treatment with gluconic acid. The TMTX gluconate salt can be converted into the desired TMTX salt by treatment with the conjugate acid of that salt. Examples for the preparation of the various salts are given below.

Trimetrexate gluconate can be converted into trimetrexate acetate hydrate by treating the trimetrexate gluconate salt with a combination of excess of acetic acid and sodium acetate and at a temperature range from 70 to 80° C. The resulting trimetrexate acetate is then crystallized by cooling to a temperature ranging from 20 to 25° C., filtered and washed with acetic acid solution in a concentration range of from 3 to 7%, or another suitable solvent that avoids solvent losses during washing. In a preferred method, the trimetrexate gluconate salt is formed using an ethanol solvent and thereafter directly converted to the acetate.

Alternatively, the trimetrexate gluconate salt may be converted to trimetrexate hydrochloride hydrate, by treating the trimetrexate gluconate salt with an excess of sodium chloride and at a temperature range from 65 to 75° C. The resulting trimetrexate hydrochloride hydrate is then crystallized by cooling to a temperature ranging from 45 to 55° C., filtered and washed with 80% ethanol in water or another suitable solvent that avoids solvent losses during washing. In a preferred method, the trimetrexate gluconate salt is formed using an aqueous solvent and thereafter directly converted to the hydrochloride.

In another alternative, the trimetrexate gluconate salt may be converted to trimetrexate methanesulfonate, by treating the trimetrexate gluconate salt with an excess of methanesulfonic acid and at a temperature range from 80 to 90° C. The resulting trimetrexate methanesulfonate is then crystallized by cooling to a temperature ranging from 15 to 25° C., filtered and washed with water or another suitable solvent that avoids solvent losses during washing. In a preferred method, the trimetrexate gluconate salt is formed using an aqueous solvent and thereafter directly converted to the methanesulfonate.

In another alternative, the trimetrexate lactate hydrate salt may be formed by direct reaction by treating the trimetrexate base with an excess aqueous lactic acid solution. The resulting trimetrexate lactate hydrate is then crystallized by cooling to a temperature ranging from 0 to 10° C., filtered and washed with aqueous ethanol in a concentration range of from 45 to 55%, or another suitable solvent that avoids solvent losses during washing.

6. EXAMPLES

Example 1

Process for Producing Crystalline Trimetrexate D(+) glucuronate hydrate

33 L of purified water was heated in a vessel to 60–70° C. 2.23 kgs (11.49 kg mol) of glucuronic acid was added to the warmed water, and 3.88 kg (10.50 kg mol) (based on the dry material) of trimetrexate base was charged. Thereafter 0.33 kgs of Tonsil was added and the mixture was pressure filtered at 50–70° C. at a pressure of about 1 bar. The filtrate was cooled to 45–50° C.

After stirring the filtrate for about 30 minutes at 45–50° C., 0.1 L of n-heptane was added. The suspension was slowly cooled to 20° C. over 1 hour, then cooled to 10° C., stirred at this temperature for 1 hour and finally cooled to 5° C.

The product was filtered off by vacuum and washed first with 3 L of a 2% solution of glucuronic acid in purified water, and then with 5 L of acetone.

A vessel was charged with 25 L of acetone and the wet trimetrexate glucuronate hydrate obtained above was charged to form a slurry. The slurry was stirred at 20–25° C. for 15 minutes and the product was again filtered off by vacuum and washed with 5 L of acetone to 7.0 kg of wet product.

The wet trimetrexate glucuronate hydrate was transferred into a cold vacuum dryer and dried at 20–30 mbar up to a maximum temperature of 50° C. for 3–6 hours to give 4.80 kg of dry trimetrexate glucuronate hydrate (78% of theoretical yield based on trimetrexate free base).

Thereafter the dried product was-sieved (500 μ) and if a tray dryer was used, also blended and filled into fiber drums with double PE bags as the insert. DSC max=136° C. The water content was 4.26% (w/w) and the purity was assayed as 104% (w/w) by HPLC with reference to the anhydrous substance.

Figure 1:
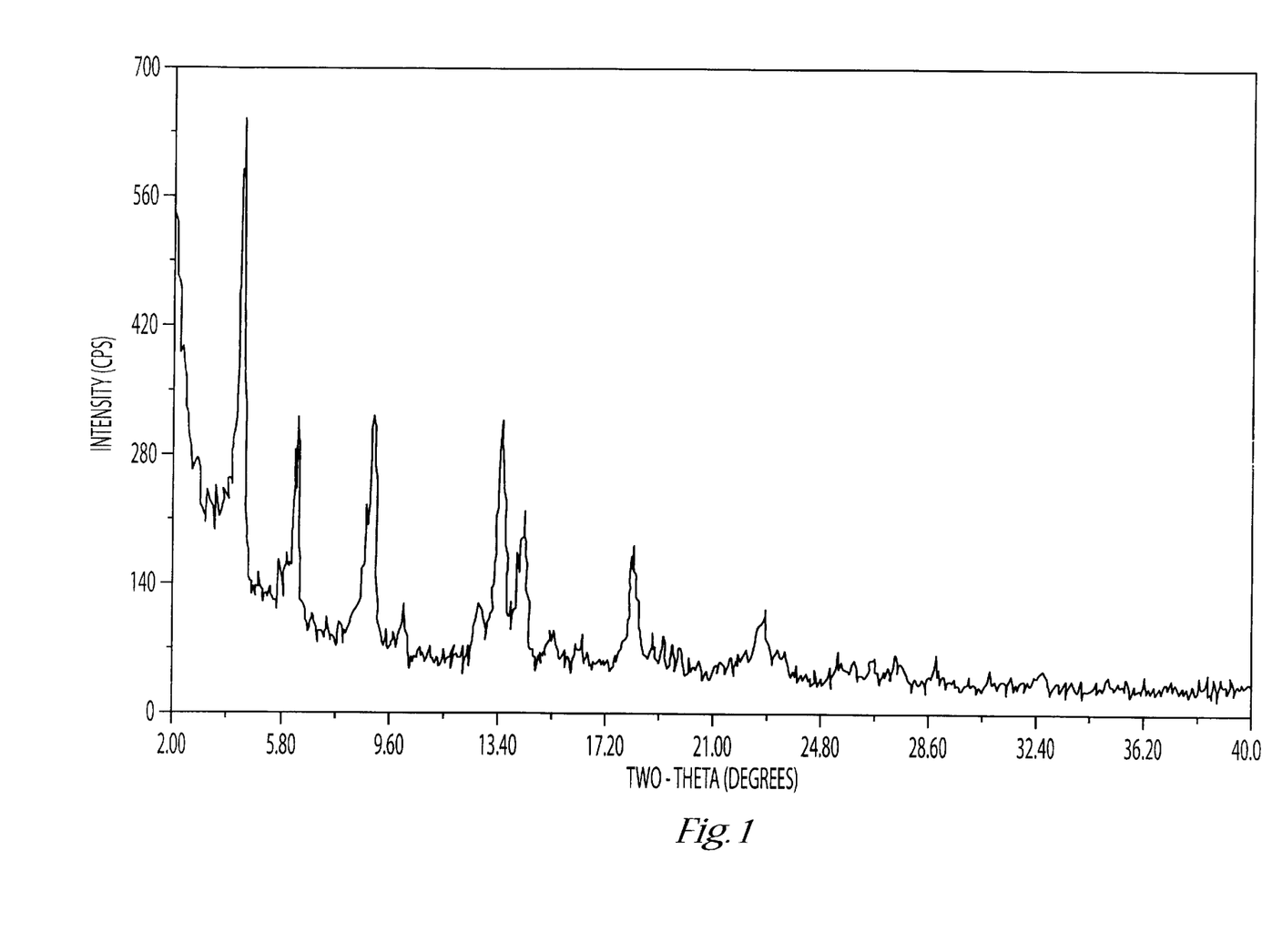
FIG. 1 exhibits the x-ray powder diffraction pattern of crystalline trimetrexate glucuronate hydrate salt of the present invention. The salt is crystalline, exhibiting measurable diffraction peaks. Cu radiation (1.54 Å) is the x-ray source.
Figure 2:
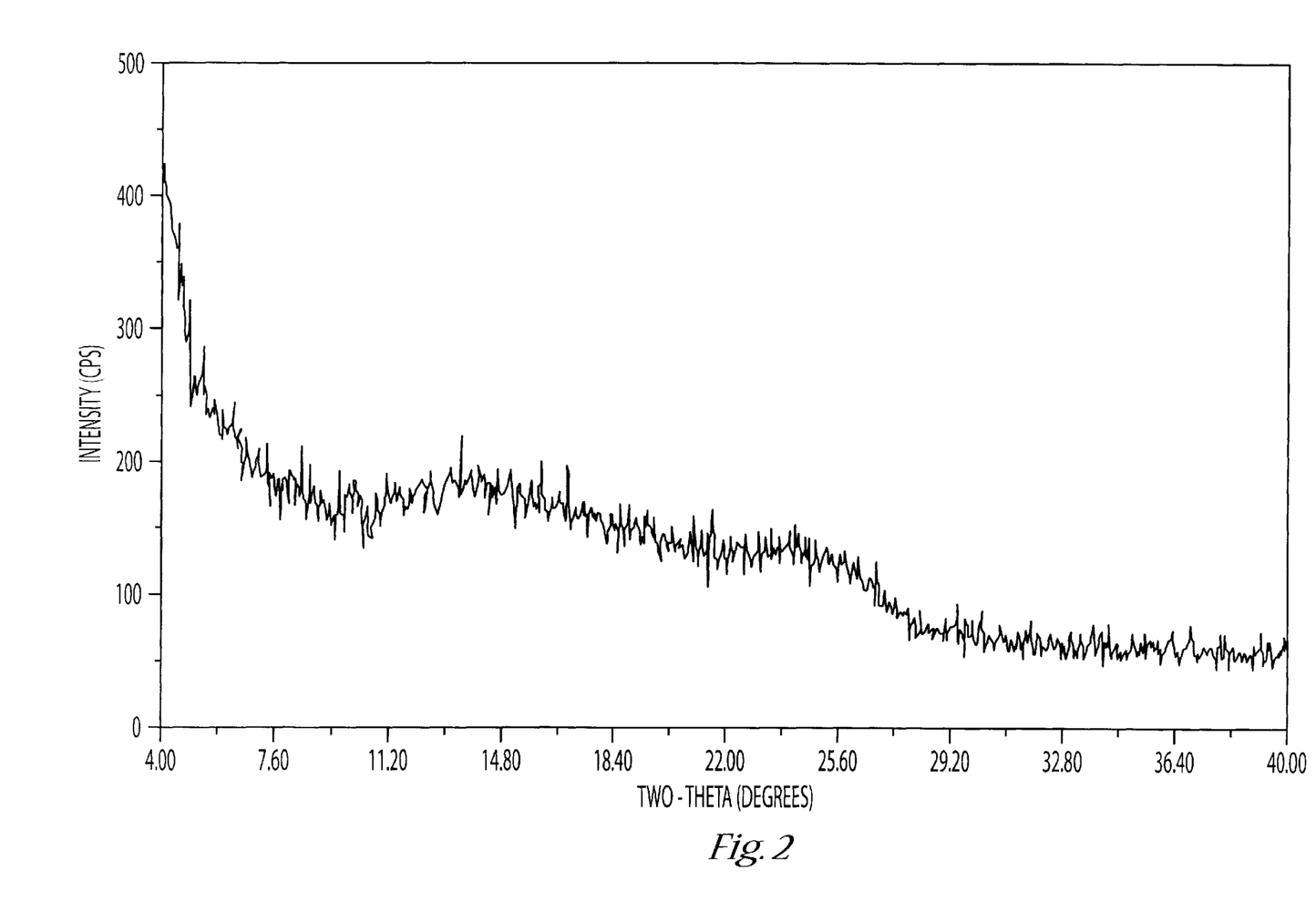
FIG. 2 exhibits the x-ray powder diffraction pattern of amorphous trimetrexate glucuronate salt produced by lyophilization. This salt exhibits no diffraction peaks and contains a hump in the two-theta range of 10–30° which is characteristic of an amorphous material. Cu radiation (1.54 Å) is the x-ray source.
Figures 3, 4:
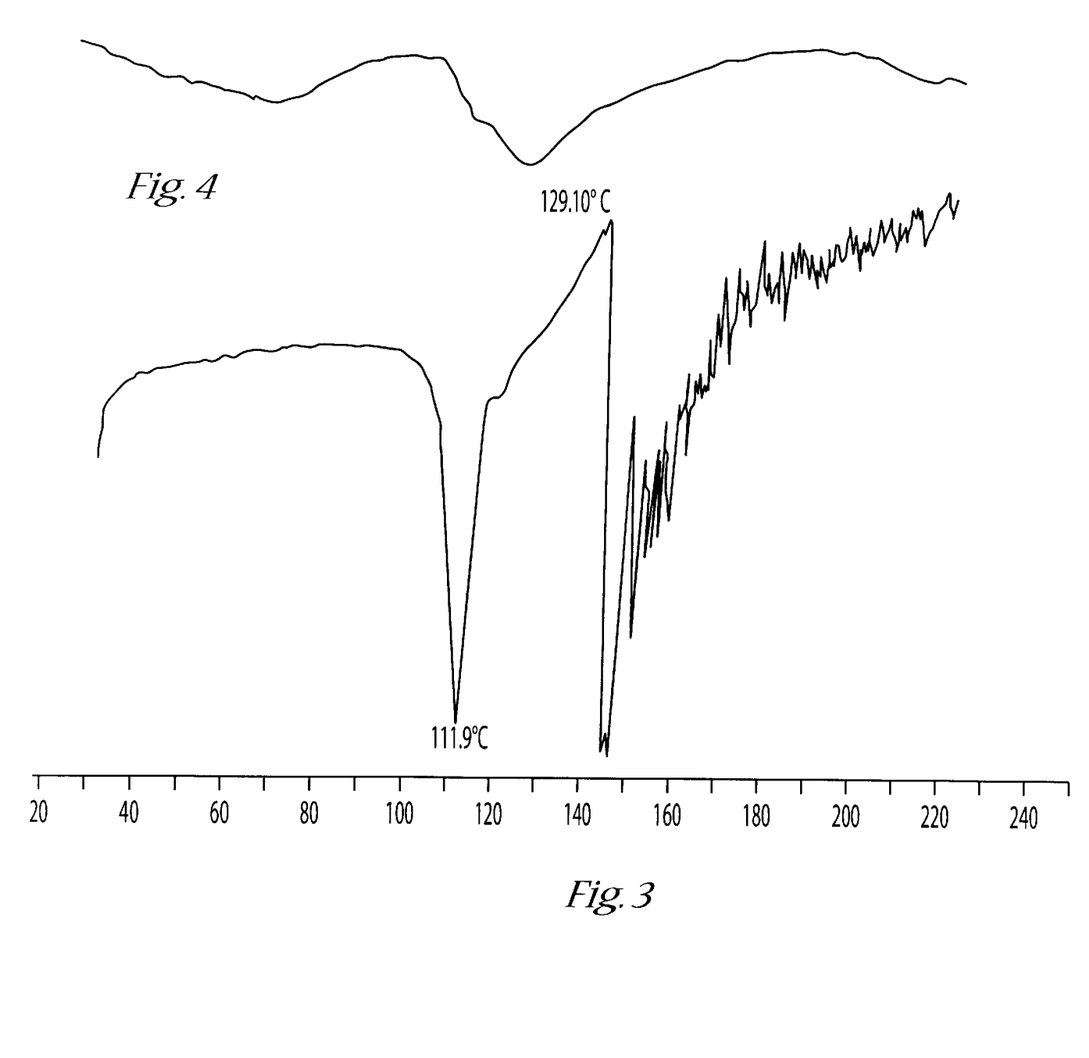
FIG. 3 exhibits the differential scanning calorimetry scan of crystalline trimetrexate glucuronate hydrate salt of the present invention. The salt exhibits a sharp melting point at approximately 136° C., closely followed by decomposition.
FIG. 4 exhibits the differential scanning calorimetry scan of amorphous trimetrexate glucuronate salt produced by lyophilization. tpThis salt exhibits a broad melting range centered at 129° C. and appears to decompose at high temperature at a slower rate.

The dry product of trimetrexate glucuronate hydrate salt exhibits an x-ray powder diffraction pattern shown in FIG. 1 and a differential scanning calorimetry scan shown in FIG. 3. Additionally, a sample of the dry product prepared as a mineral oil dispersion exhibits birefringence typical of crystalline materials.

Example 2
Process for Producing Trimetrexate Acetate Hydrate 62.0 g of Trimetrexate base hydrate (160 mMol) were slurried in 350 ml of ethanol and 100 ml of water. The mixture was heated to 70° C. and 28 ml of a 50% aqueous gluconic acid solution (90 mMol), 7.5 ml of glacial acetic acid, 4 g of Tonsil and 0.5 g of activated charcoal were added. The mixture was then pressure filtered at 70–75° C.

The clear brown solution was then charged with a solution of 6.5 g (80 mMol) of sodium acetate in 25 ml of water and then with 11 ml of glacial acetic acid at 70–75° C.

The mixture was then cooled to 20° C. The coarsely crystalline precipitate of the acetate salt was filtered off via a nutsche filter and washed with 50 ml of a 5% aqueous solution of acetic acid. After drying in a vacuum oven at 75° C., 65.5 g (84% of the theoretical yield) of dark-yellow crystals were obtained. DSCmax=128° C. (—H$_2$O), min= 209° C., 217° C. The water content was 4.1% (w/w) and the purity was assayed at 99.3%, (w/w) by titration with reference to the anhydrous substance.

Figure 5:
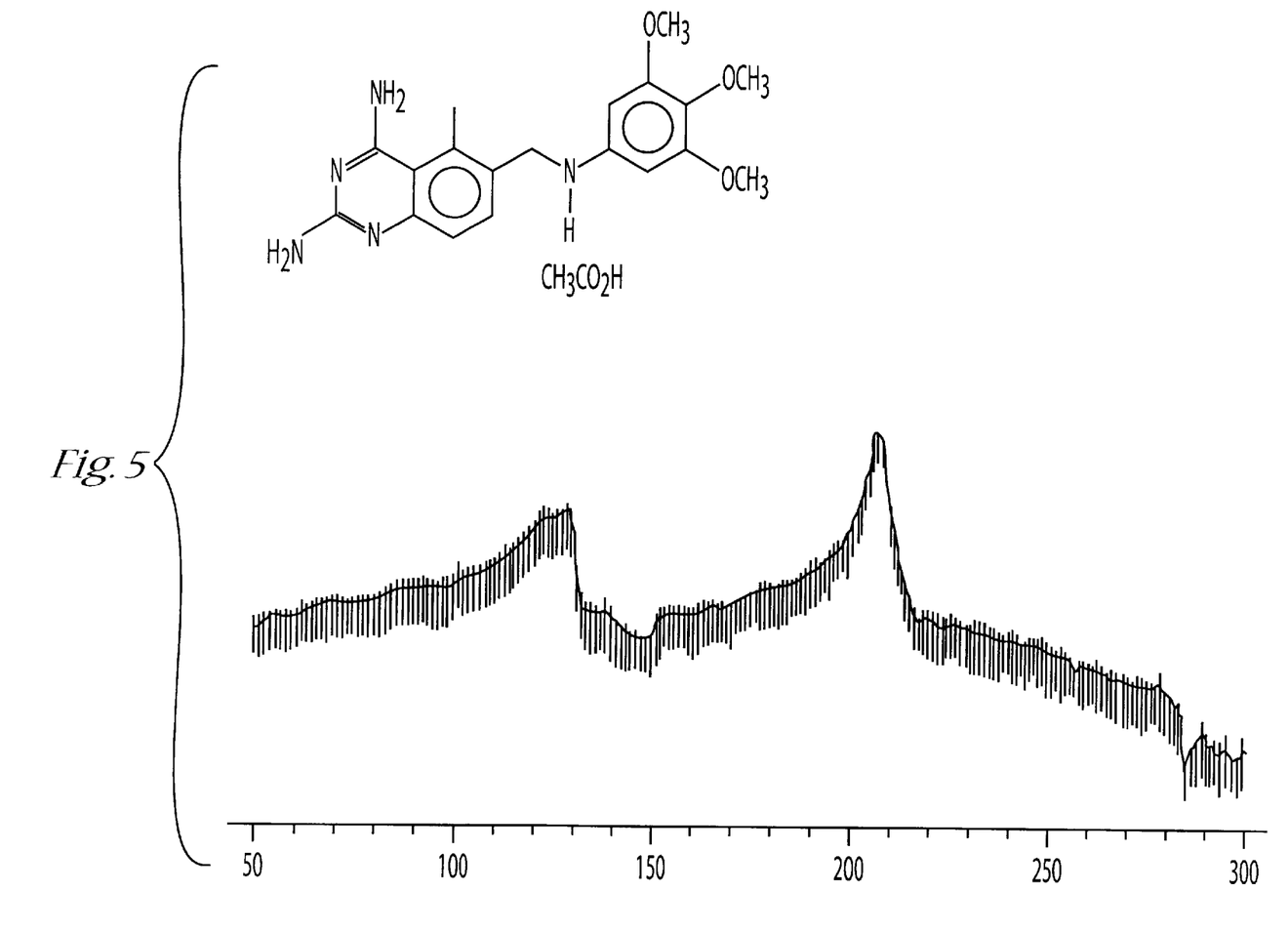
FIG. 5 exhibits the differential scanning colorimetry scan of crystalline trimetrexate acetate hydrate salt of the present invention.
Figure 6:
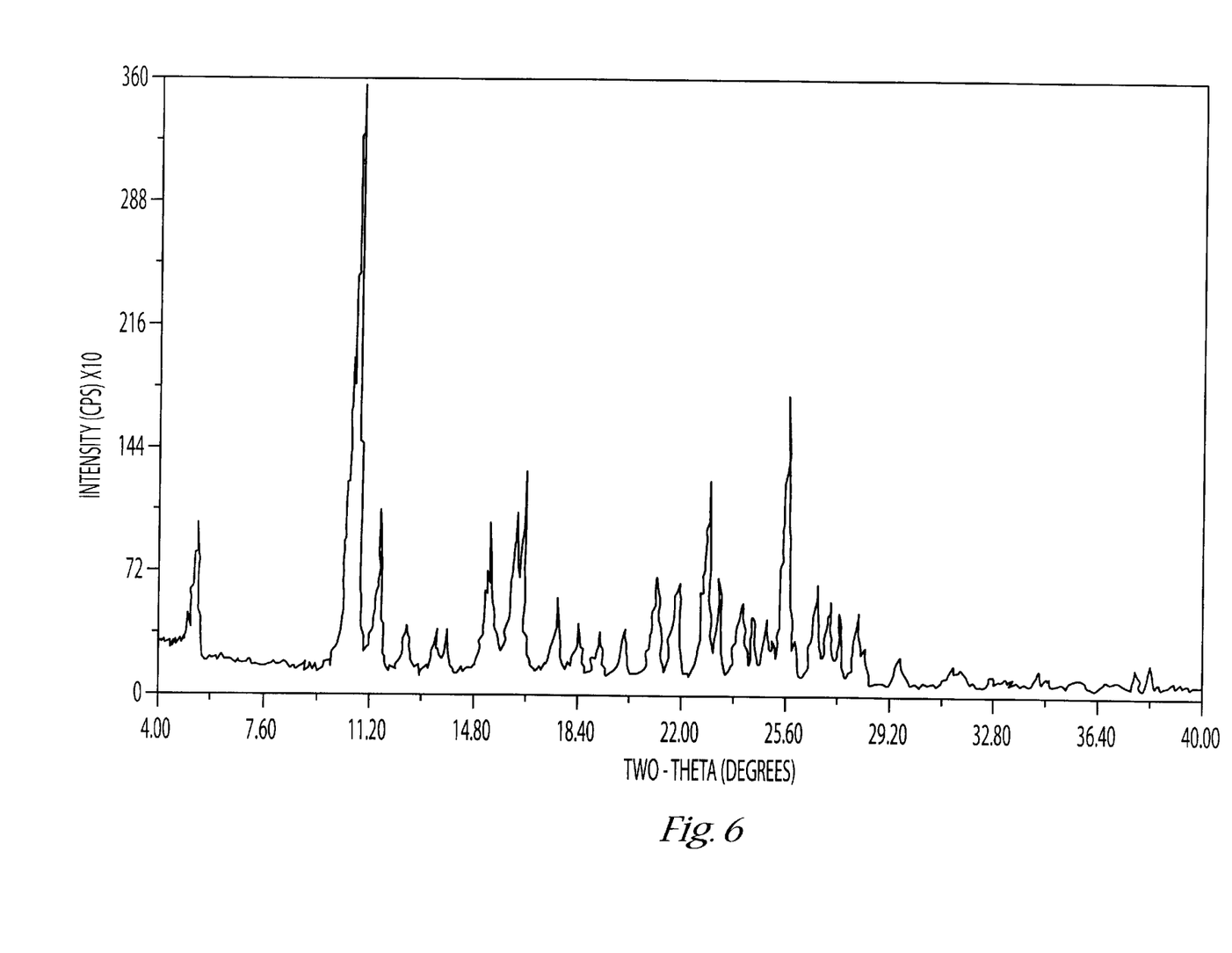
FIG. 6 exhibits the x-ray powder diffraction pattern of crystalline trimetrexate acetate hydrate salt of the present invention. Cu radiation (1.54 Å) is the x-ray source.

The dry product of trimetrexate acetate hydrate exhibits the differential scanning colorimetry scan shown in FIG. 5, and the x-ray powder-diffraction pattern shown in FIG. 6.

Example 3
Process for Producing Trimetrexate Hydrochloride Hydrate 50 g of Trimetrexate base hydrate (130 mmol) were slurried in 500 ml of water and 72 ml of a 50% aqueous gluconic acid solution. The mixture was heated to 70° C. and stirred until a homogeneous solution was obtained. After the addition of 1 g of activated charcoal the mixture was pressure filtered and cooled to 50° C.

Figure 7:
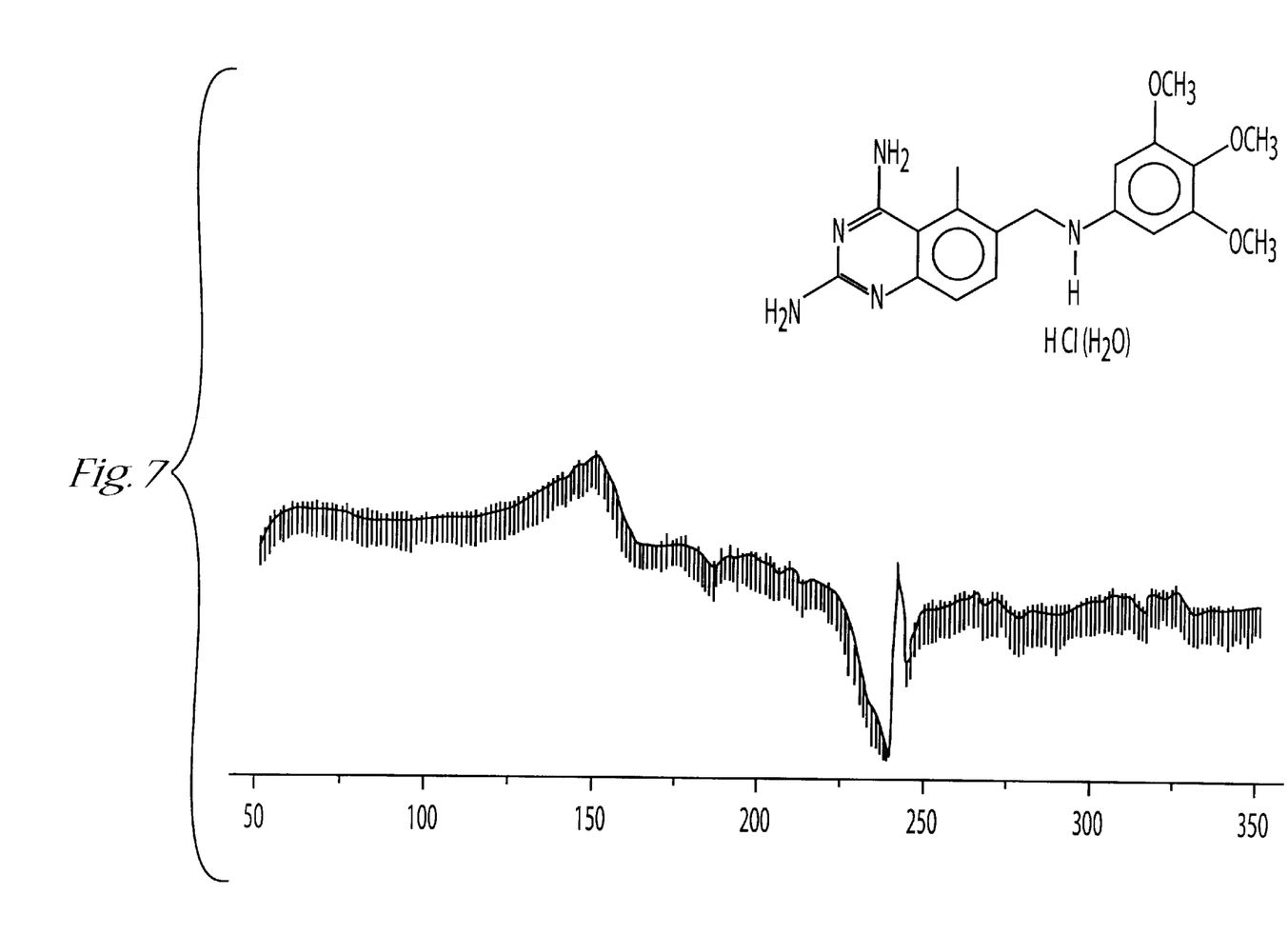
FIG. 7 exhibits the differential scanning colorimetry scan of crystalline trimetrexate hydrochloride hydrate salt of the present invention.
Figure 8:
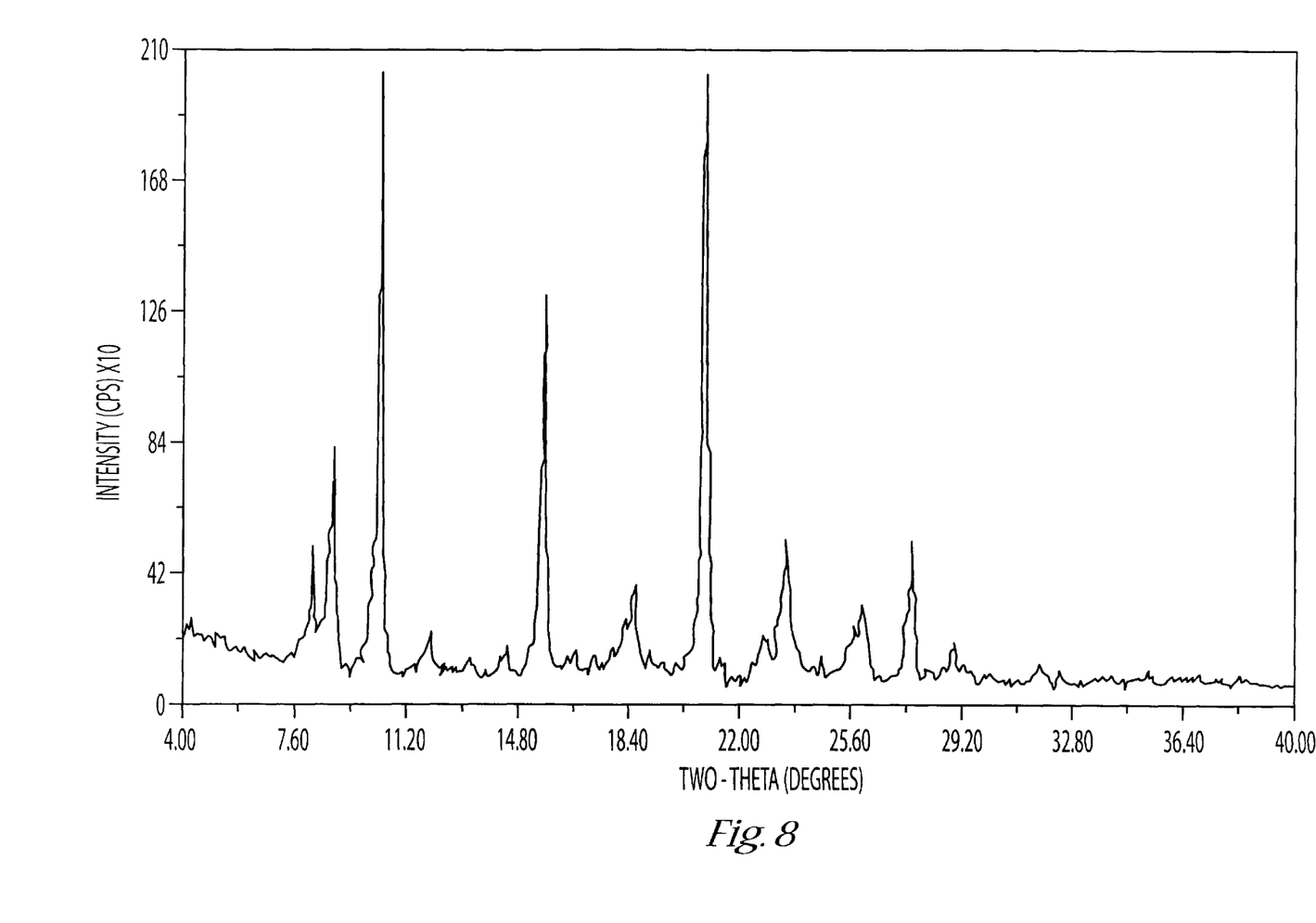
FIG. 8 exhibits the x-ray powder diffraction pattern of crystalline trimetrexate hydrochloride hydrate salt of the present invention. Cu radiation (1.54 Å) is the x-ray source.

20 g of sodium chloride was added. The solution was then cooled to 20° C. and stirred for one hour. The crystals were filtered off on a nutsche filter and washed two times with 50 ml of 80% ethanol. After drying in a vacuum oven at 75° C. 48 g (90% of the theoretical yield) of the hydrochloride salt was obtained. DSCmax=148° C., min=233° C. The water content was 5.9% (w/w) and the purity was assayed at 98.7% (w/w) by titration with reference to the anhydrous substance. The dry product of trimetrexate hydrochloride hydrate exhibits the differential scanning colorimetry scan shown in FIG. 7, and the x-ray powder diffraction pattern shown in FIG. 8.

Example 4
Process for Producing Trimetrexate Methanesulfonate 77 g (200 mmol) of Trimetrexate base hydrate were slurried in 700 ml of deionized water. To the suspension were added 100 ml of 50% aqueous gluconic acid solution, 5 g of Tonsil and 5 g of activated charcoal. The mixture was heated to 50° C. and pressure filtered.

The filtrate was then heated to 80° C. and charged with 26.4 ml (400 mmol) of methanesulfonic acid). In.the range of 80 to 90° C., a solution of 30 ml of 30% sodium hydroxide in 100 ml of water was added to adjust the pH to 4.2. After crystallization of the colorless methanesulfonate, the solution was cooled to 20° C. The solid was filtered off on a nutsche filter and washed with water. After drying to a constant weight in a vacuum oven at 75 to 90° C., 89 g (95% of the theoretical yield) was obtained. DSCmax=239° C., min=241° C. and 290° C. The water content was 0.2% (w/w) and the purity was assayed as 99.2% (w/w) by titration with reference to the anhydrous substance.

Figure 9:
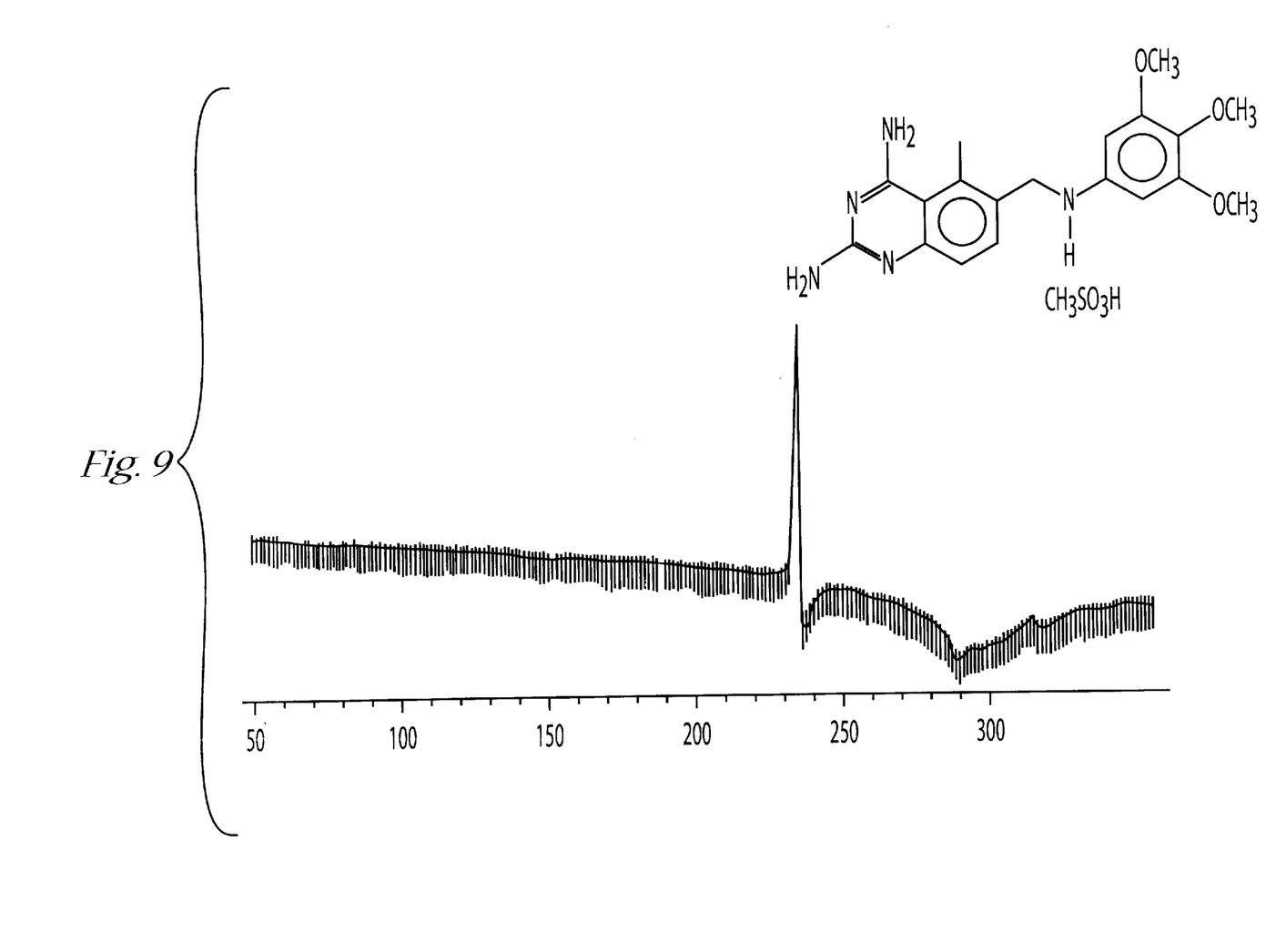
FIG. 9 exhibits the differential scanning colorimetry scan of crystalline trimetrexate methanesulfonate salt of the present invention.
Figure 10:
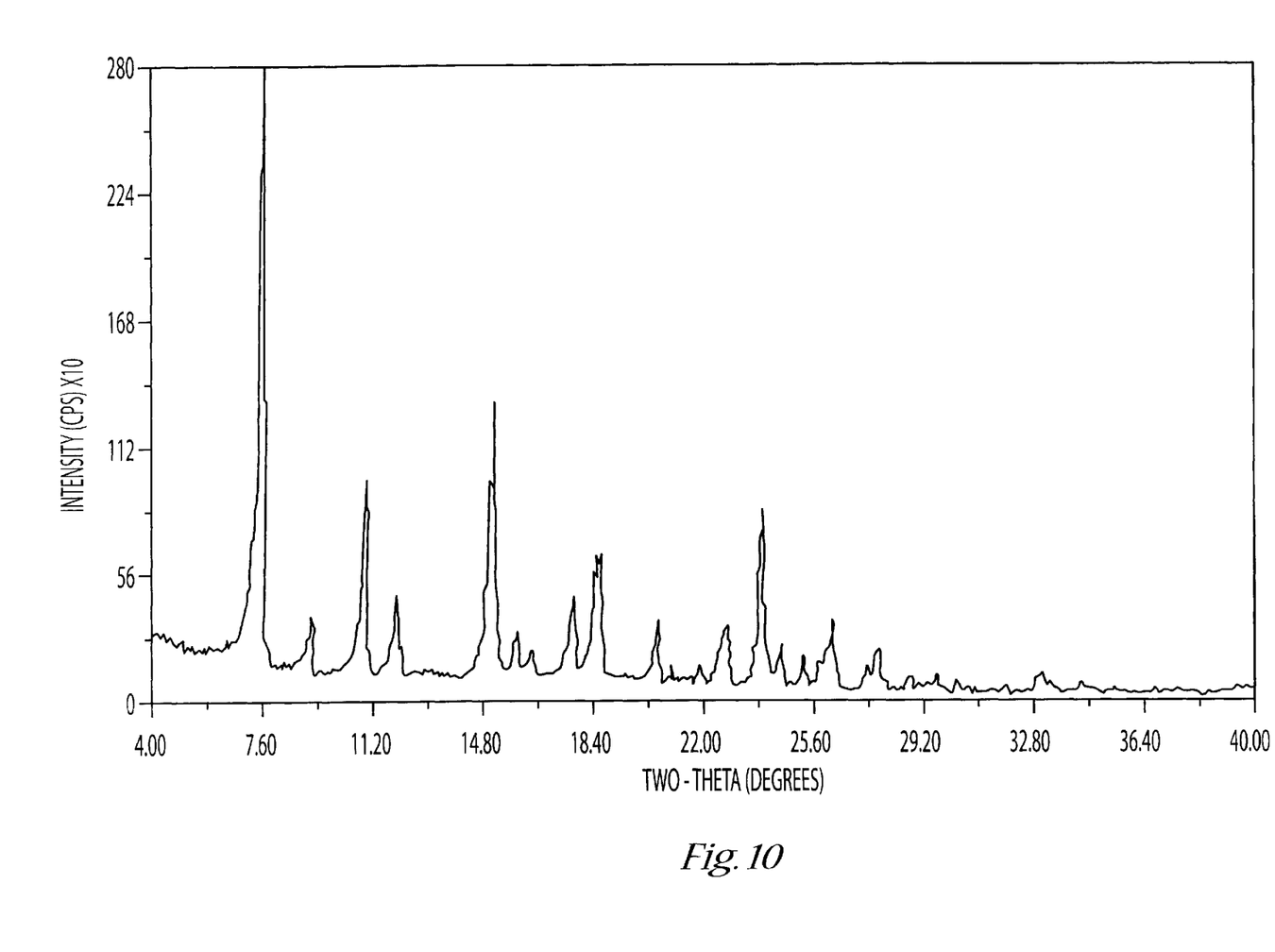
FIG. 10 exhibits the x-ray powder diffraction pattern of crystalline trimetrexate methanesulfonate salt of the present invention. Cu radiation (1.54 Å) is the x-ray source.

The dry product of trimetrexate methanesulfonate exhibits the differential scanning colorimetry scan shown in FIG. 9, and the x-ray powder diffraction pattern shown in FIG. 10.

Example 5
Process for Producing Trimetrexate Lactate Hydrate 13 g (34 mMol) of Trimetrexate base hydrate and 3.5 ml of an 85% aqueous solution of L-(+)-lactic acid (40 mMol) were dissolved in 100 ml of water by heating to 40° C. A pressure filter filtration with 1 g of activated charcoal and 1 g of Tonsil was performed at this temperature.

100 ml of ethanol were added to the filtrate and the mixture was then cooled to 5° C. The precipitated solid was filtered off and washed with 20 ml of 50% aqueous ethanol.

After drying in vacuo at 75° C. 13.1 g (81% of the theoretical yield) of the pale yellow lactate salt was obtained. DSCmax=196° C. and 208° C., min=198° C. The water content was 3.3% (w/w) and the purity was assayed as 99.2% (wlw) by titration with reference to the anhydrous substance.

Figure 11:
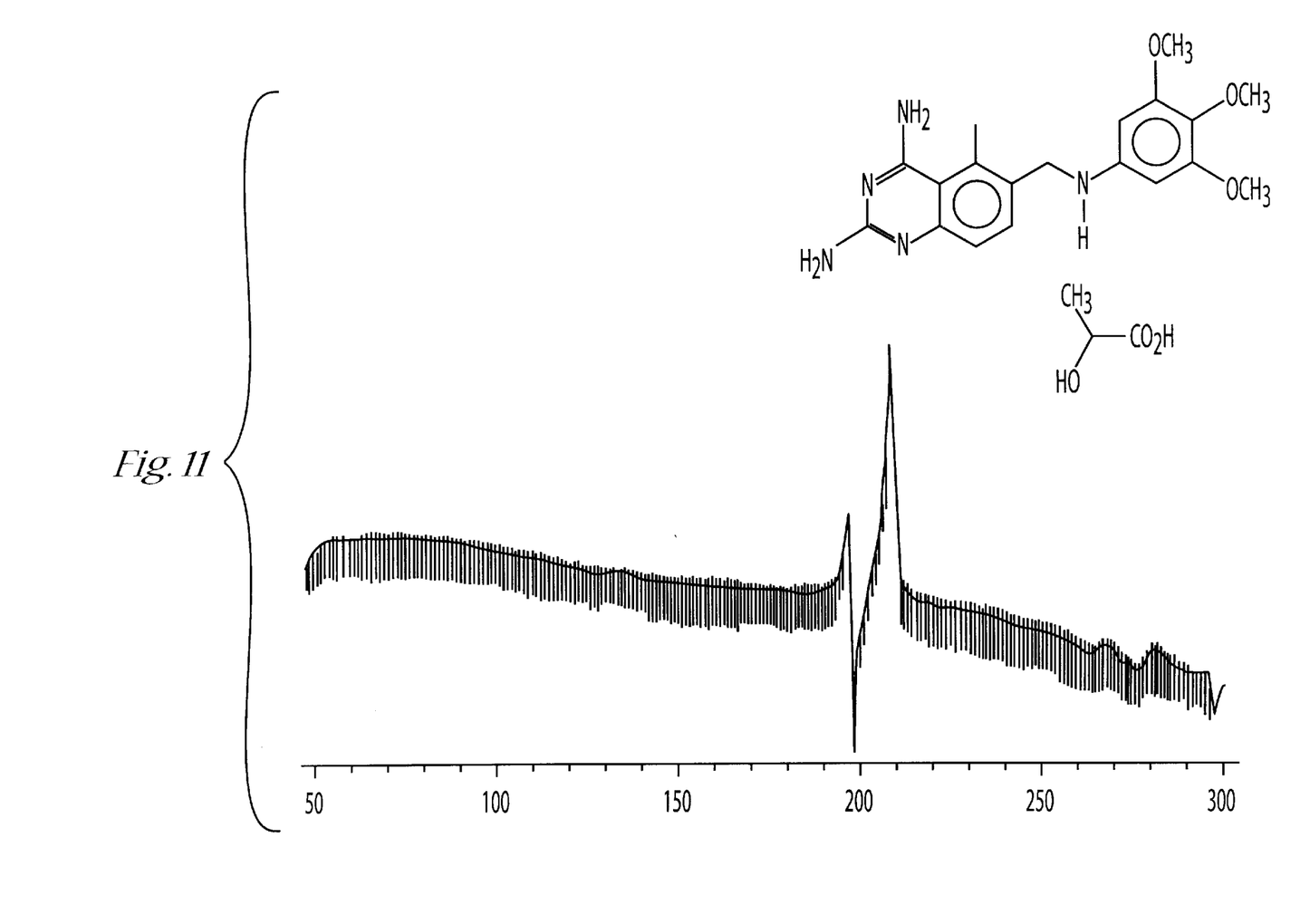
FIG. 11 exhibits the differential scanning colorimetry scan of crystalline trimetrexate lactate hydrate salt of the present invention.
Figure 12:
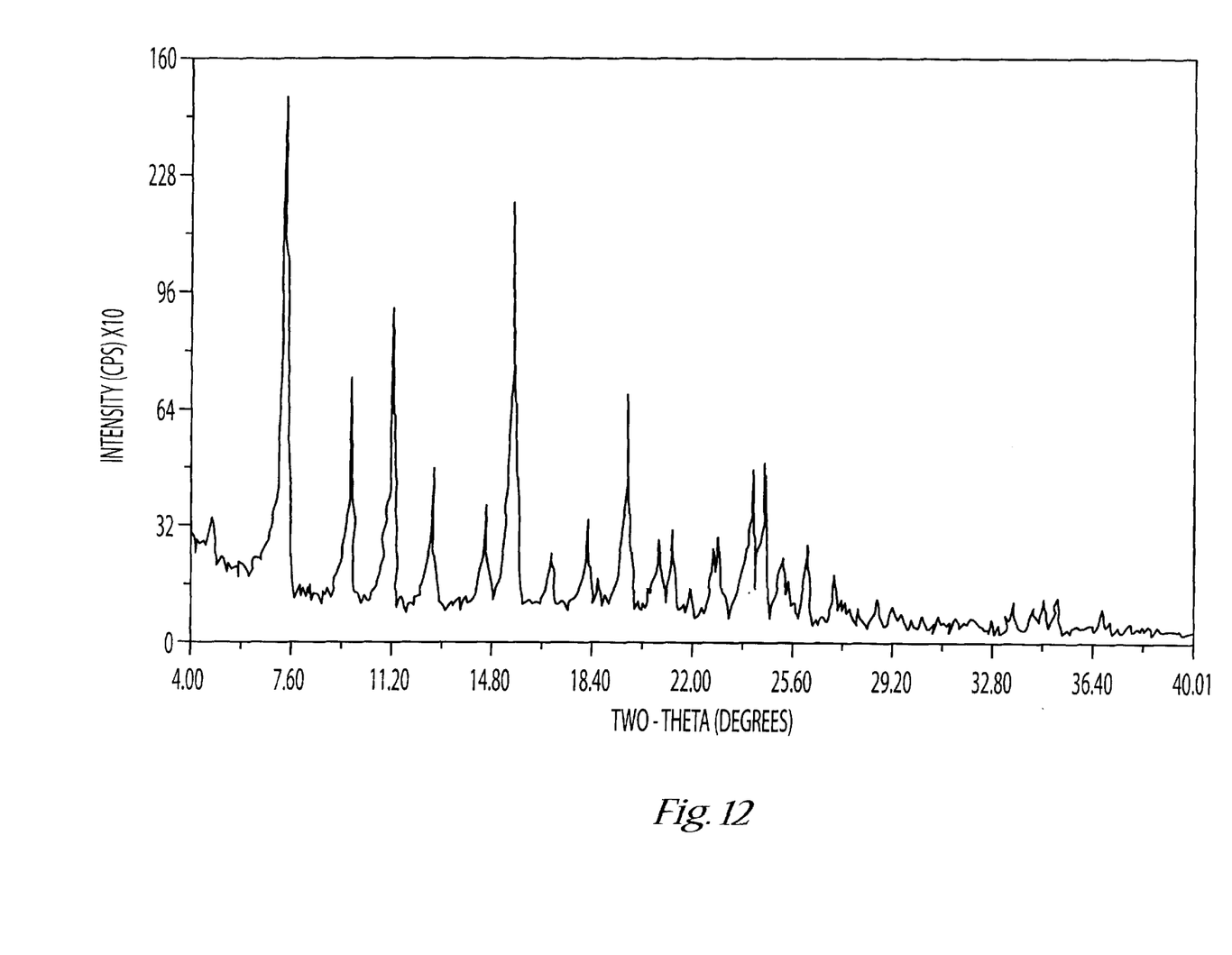
FIG. 12 exhibits the x-ray powder diffraction pattern of crystalline trimetrexate lactate hydrate salt of the present invention. Cu radiation (1.54 Å) is the x-ray source.

The dry product of trimetrexate lactate hydrate exhibits the differential scanning colorimetry scan shown in FIG. 11, and the x-ray powder diffraction pattern shown in FIG. 12.

PARAMETERS

Molar ratios for raw materials and reagents vary typically ±3%

A ±5% variation is an operational allowance for all solvent measurements unless otherwise stated.

The additions "about" and "approx." indicate that the quantities may vary in a broader range.

Times are approximate and may vary ±5% unless otherwise stated.

Tolerance for temperature is ±5° C. unless otherwise stated.

For pressure, a variation range of ±10% is allowed unless otherwise stated.

pH may vary ±1 pH unit unless otherwise stated. If pH is exceeded during adjustment it may be corrected using an appropriate acid or base.

TABLE 1

Date: 6-DEC-93    Time: _:51:46
EXTENDED OUTPUT FROM THE PEAK LOCATE PROGRAM
Sample ID: TRIMETREXATE-GLUCORONATE BATCH NO. 93-07231
File: HEU06.RAW       D/I File: HEU06.DIF
Date & time of measurement: 03-DEC-93 10:21:49
FILE MEASUREMENT PARAMETERS:
RANGE #1    Start angle:    Stop angle:    Step:    Count time:
            2.000           80.000         0.050
Diffractometer: 1-A    Scan: STEP SCAN
Specified parameters:       Method = Trend-oriented
Sensitivity factor = 2.00
The smallest peak relative to the largest = 0.50%
Alpha-2 removal
Alpha-1/alpha-2 ratio = 2.00
Calibration of 2-theta
SERIES # 1

| No | 2Theta | d | Rel I (%) | Max I | Integ I | Width | Type |
|---|---|---|---|---|---|---|---|
| Range # 1 | | | | | | | |
| 1 | 4.473 | 19.7411 | 100.0 | 309. | 1531.94 | 0.248 | KA1 |
| 2 | 6.348 | 13.9127 | 41.5 | 128. | 468.33 | 0.182 | KA1 |
| 3 | 8.990 | 9.8289 | 51.6 | 160. | 1210.00 | 0.379 | KA1 |
| 4 | 10.086 | 8.7627 | 12.6 | 39. | 176.94 | 0.228 | KA1 |
| 5 | 12.711 | 6.9584 | 9.3 | 29. | 198.89 | 0.344 | KA1 |
| 6 | 13.517 | 6.5454 | 51.1 | 158. | 1063.61 | 0.336 | KA1 |
| 7 | 14.286 | 6.1949 | 30.8 | 95. | 574.17 | 0.301 | KA1 |
| 8 | 16.290 | 5.4369 | 6.5 | 20. | 112.78 | 0.281 | KA1 |
| 9 | 18.061 | 4.9075 | 27.0 | 84. | 589.44 | 0.353 | KA1 |
| 10 | 22.698 | 3.9145 | 10.2 | 31. | 179.44 | 0.286 | KA1 |
| 11 | 69.486 | 1.3516 | 3.8 | 12. | 32.22 | 0.138 | KA1 |

TABLE 2

Date: 22-DEC-94    Time: 12:47:38
EXTENDED OUTPUT FROM THE PEAK LOCATE PROGRAM
Sample ID: LOT 92-11926
File: USB27.RAW       D/I File: USB27.DIF
Date & time of measurement: 22-DEC-94 11:36:33
FILE MEASUREMENT PARAMETERS:
RANGE #1    Start angle:    Stop angle:    Step:    Count time:
            4.000           40.000         0.050
Diffractometer: 1-A    Scan: STEP SCAN
Specified parameters:       Method = Trend-oriented
Sensitivity factor = 2.00
The smallest peak relative to the largest = 0.50%
Alpha-2 removal
Alpha-1/alpha-2 ratio = 2.00
Calibration of 2-theta
SERIES # 1

| No | 2Theta | d | Rel I (%) | Max I | Integ I | Width | Type |
|---|---|---|---|---|---|---|---|
| Range # 1 | | | | | | | |
| 1 | 5.049 | 17.4873 | 3.0 | 66. | 94.44 | 0.071 | KA1 |
| 2 | 5.401 | 16.3488 | 19.8 | 441. | 1377.22 | 0.156 | KA1 |
| 3 | 10.604 | 8.3359 | 54.9 | 1218. | 4812.06 | 0.221 | KA1 |
| 4 | 10.800 | 8.1851 | 100.0 | 2221. | 7485.72 | 0.169 | KA1 |
| 5 | 11.592 | 7.6278 | 27.4 | 609. | 2614.17 | 0.215 | KA1 |
| 6 | 12.504 | 7.0731 | 7.5 | 166. | 570.00 | 0.172 | KA1 |
| 7 | 13.546 | 6.5315 | 5.1 | 114. | 438.06 | 0.192 | KA1 |
| 8 | 13.900 | 6.3660 | 6.0 | 133. | 366.67 | 0.138 | KA1 |
| 9 | 15.077 | 5.8717 | 6.0 | 134. | 332.78 | 0.124 | KA1 |
| 10 | 15.353 | 5.7664 | 19.5 | 434. | 1590.28 | 0.183 | KA1 |
| 11 | 16.234 | 5.4555 | 24.4 | 543. | 2397.11 | 0.238 | KA1 |
| 12 | 16.500 | 5.3682 | 35.7 | 794. | 2926.23 | 0.184 | KA1 |
| 13 | 17.674 | 5.0143 | 11.5 | 256. | 893.33 | 0.174 | KA1 |
| 14 | 18.416 | 4.8137 | 6.9 | 153. | 525.00 | 0.171 | KA1 |
| 15 | 19.167 | 4.6269 | 5.9 | 130. | 367.78 | 0.141 | KA1 |
| 16 | 20.049 | 4.4253 | 7.8 | 173. | 785.56 | 0.227 | KA1 |
| 17 | 21.140 | 4.1992 | 16.1 | 357. | 2059.44 | 0.289 | KA1 |
| 18 | 21.679 | 4.0961 | 7.0 | 156. | 200.35 | 0.116 | KA1 |
| 19 | 21.896 | 4.0560 | 16.9 | 376. | 1767.43 | 0.235 | KA1 |

TABLE 2-continued

| 20 | 22.902 | 3.8801 | 31.8 | 707. | 3481.67 | 0.246 | KA1 |
|---|---|---|---|---|---|---|---|
| 21 | 23.312 | 3.8126 | 14.8 | 329. | 1003.33 | 0.152 | KA1 |
| 22 | 23.998 | 3.7052 | 9.0 | 199. | 871.99 | 0.242 | KA1 |
| 23 | 24.105 | 3.6890 | 12.0 | 267. | 771.34 | 0.144 | KA1 |
| 24 | 24.507 | 3.6294 | 8.4 | 186. | 461.39 | 0.124 | KA1 |
| 25 | 24.963 | 3.5642 | 6.0 | 134. | 353.33 | 0.132 | KA1 |
| 26 | 25.216 | 3.5290 | 2.3 | 51. | 126.11 | 0.123 | KA1 |
| 27 | 25.657 | 3.4694 | 45.7 | 1015. | 5032.78 | 0.248 | KA1 |
| 28 | 26.722 | 3.3334 | 13.8 | 305. | 1221.94 | 0.200 | KA1 |
| 29 | 27.198 | 3.2761 | 10.3 | 228. | 805.56 | 0.177 | KA1 |
| 30 | 27.548 | 3.2353 | 10.0 | 222. | 671.39 | 0.151 | KA1 |
| 31 | 28.140 | 3.1686 | 8.4 | 187. | 606.99 | 0.175 | KA1 |
| 33 | 29.541 | 3._214 | 1.4 | 31. | 51.67 | 0.082 | KA1 |
| 34 | 31.471 | 2._403 | 1.2 | 27. | 92.22 | 0.168 | KA1 |
| 35 | 34.406 | 2.6045 | 2.5 | 55. | 179.72 | 0.163 | KA1 |
| 36 | 37.820 | 2.3769 | 2.9 | 64. | 270.00 | 0.209 | KA1 |
| 37 | 38.356 | 2.3449 | 3.8 | 84. | 281.39 | 0.168 | KA1 |

USB27. RAW

TABLE 3

Date: 22-DEC-94    Time: 12:49:55
EXTENDED OUTPUT FROM THE PEAK LOCATE PROGRAM
Sample ID: LOT 92-11927
File: USB28.RAW       D/I File: USB28.DIF
Date & time of measurement: 22-DEC-94 11:59:09
FILE MEASUREMENT PARAMETERS:
RANGE #1    Start angle:    Stop angle:    Step:    Count time:
            4.000           40.000         0.050    1
Diffractometer: 1-A    Scan: STEP SCAN
Specified parameters:       Method = Trend-oriented
Sensitivity factor = 2.00
The smallest peak relative to the largest = 0.50%
Alpha-2 removal
Alpha-1/alpha-2 ratio = 2.00
Calibration of 2-theta
SERIES # 1

| No | 2Theta | d | Rel I (%) | Max I | Integ I | Width | Type |
|---|---|---|---|---|---|---|---|
| Range # 1 | | | | | | | |
| 1 | 8.100 | 10.9064 | 14.2 | 181. | 555.83 | 0.153 | KA1 |
| 2 | 8.772 | 10.0726 | 33.1 | 422. | 1858.33 | 0.220 | KA1 |
| 3 | 10.357 | 8.5341 | 100.0 | 1277. | 5850.56 | 0.229 | KA1 |
| 4 | 11.910 | 7.4249 | 3.0 | 39. | 56.39 | 0.073 | KA1 |
| 5 | 15.182 | 5.8310 | 1.4 | 18. | 56.11 | 0.155 | KA1 |
| 6 | 15.568 | 5.6873 | 61.3 | 783. | 3116.94 | 0.199 | KA1 |
| 7 | 17.299 | 5.1221 | 2.9 | 37. | 110.28 | 0.150 | KA1 |
| 8 | 18.539 | 4.7821 | 9.3 | 119. | 508.06 | 0.214 | KA1 |
| 9 | 19.055 | 4.6538 | 1.7 | 22. | 130.00 | 0.069 | KA1 |
| 10 | 20.811 | 4.2648 | 98.1 | 1252. | 5814.44 | 0.232 | KA1 |
| 11 | 21.397 | 4.1494 | 2.9 | 37. | 86.11 | 0.117 | KA1 |
| 12 | 22.658 | 3.9213 | 1.1 | 14. | 25.28 | 0.092 | KA1 |
| 13 | 22.893 | 3.8816 | 2.0 | 25. | 68.89 | 0.137 | KA1 |
| 14 | 23.424 | 3.7947 | 18.6 | 237. | 1412.78 | 0.298 | KA1 |
| 15 | 25.393 | 3.5048 | 2.9 | 37. | 61.11 | 0.083 | KA1 |
| 16 | 25.917 | 3.4350 | 5.1 | 65. | 143.19 | 0.155 | KA1 |
| 17 | 26.030 | 3.4204 | 7.2 | 92. | 338.75 | 0.185 | KA1 |
| 18 | 27.510 | 3.2397 | 21.9 | 280. | 1365.56 | 0.244 | KA1 |
| 19 | 28.824 | 3.0949 | 5.3 | 68. | 241.67 | 0.178 | KA1 |
| 20 | 31.541 | 2.8342 | 0.5 | 6. | 26.67 | 0.207 | KA1 |

USB28. RAW
CONT.

TABLE 4

Date: 22-DEC-94    Time: 13:07:28
EXTENDED OUTPUT FROM THE PEAK LOCATE PROGRAM
Sample ID: LOT 92-11929
File: USB30.RAW       D/I File: USB30.DIF
Date & time of measurement: 22-DEC-94 12:41:39
FILE MEASUREMENT PARAMETERS:
RANGE #1    Start angle:    Stop angle:    Step:    Count time:
            4.000           40.000         0.050

TABLE 4-continued

Diffractometer: 1-A  Scan: STEP SCAN
Specified parameters:  Method = Trend-oriented
Sensitivity factor = 2.00
The smallest peak relative to the largest = 0.50%
Alpha-2 removal
Alpha-1/alpha-2 ratio = 2.00
Calibration of 2-theta
SERIES # 1

| No | 2Theta | d | Rel I (%) | Max I | Integ I | Width | Type |
|---|---|---|---|---|---|---|---|
| Range # 1 | | | | | | | |
| 1 | 7.541 | 11.7132 | 100.0 | 1725. | 7379.44 | 0.214 | KA1 |
| 2 | 9.196 | 9.6093 | 9.2 | 158. | 617.78 | 0.195 | KA1 |
| 3 | 11.007 | 8.0317 | 32.0 | 553. | 2370.00 | 0.214 | KA1 |
| 4 | 12.036 | 7.3475 | 12.1 | 208. | 810.56 | 0.195 | KA1 |
| 5 | 15.159 | 5.8401 | 47.0 | 811. | 4142.64 | 0.257 | KA1 |
| 6 | 15.337 | 5.7724 | 13.1 | 226. | 480.14 | 0.106 | KA1 |
| 7 | 15.993 | 5.5372 | 6.7 | 116. | 381.67 | 0.164 | KA1 |
| 8 | 16.473 | 5.3770 | 3.7 | 64. | 211.67 | 0.165 | KA1 |
| 9 | 17.799 | 4.9794 | 13.0 | 224. | 978.33 | 0.218 | KA1 |
| 10 | 18.521 | 4.7867 | 19.2 | 331. | 1376.16 | 0.225 | KA1 |
| 11 | 18.657 | 4.7521 | 19.8 | 342. | 942.73 | 0.138 | KA1 |
| 12 | 20.571 | 4.3140 | 9.5 | 165. | 508.33 | 0.154 | KA1 |
| 13 | 21.060 | 4.2150 | 1.9 | 32. | 59.44 | 0.092 | KA1 |
| 14 | 22.744 | 3.9067 | 9.1 | 157. | 710.92 | 0.241 | KA1 |
| 15 | 22.856 | 3.8878 | 9.0 | 155. | 339.91 | 0.110 | KA1 |
| 16 | 23.969 | 3.7096 | 29.1 | 502. | 2503.89 | 0.249 | KA1 |
| 17 | 24.653 | 3.6083 | 4.4 | 76. | 191.94 | 0.126 | KA1 |
| 18 | 25.405 | 3.5032 | 5.1 | 87. | 342.22 | 0.196 | KA1 |
| 19 | 25.988 | 3.4258 | 2.1 | 36. | 107.50 | 0.147 | KA1 |
| 20 | 26.328 | 3.3823 | 9.3 | 161. | 685.00 | 0.212 | KA1 |
| 21 | 27.503 | 3.2405 | 2.8 | 48. | 143.61 | 0.151 | KA1 |
| 22 | 27.832 | 3.2030 | 4.7 | 82. | 360.00 | 0.221 | KA1 |
| 23 | 28.906 | 3.0863 | 2.7 | 46. | 131.39 | 0.142 | KA1 |
| 24 | 29.807 | 2.9950 | 2.2 | 37. | 71.11 | 0.095 | KA1 |
| 25 | 30.463 | 2.9320 | 1.7 | 29. | 60.56 | 0.103 | KA1 |
| 26 | 33.219 | 2.6948 | 2.0 | 34. | 120.56 | 0.177 | KA1 |
| 27 | 34.569 | 2.5926 | 1.0 | 18. | 49.44 | 0.140 | KA1 |
| 28 | 35.656 | 2.5160 | 1.1 | 19. | 53.33 | 0.140 | KA1 |

USB30.RAW
CONT.

TABLE 5

Date: 22-DEC-94  Time: 12:53:01
EXTENDED OUTPUT FROM THE PEAK LOCATE PROGRAM
Sample ID: LOT 92-11928
File: USB29.RAW  D/I File: USB29.DIF
Date & time of measurement: 22-DEC-94 12:20:33
FILE MEASUREMENT PARAMETERS:
RANGE #1  Start angle:  Stop angle:  Step:  Count time:
  4.000  40.000  0.050  1
Diffractometer: 1-A  Scan: STEP SCAN
Specified parameters:  Method = Trend-oriented
Sensitivity factor = 2.00
The smallest peak relative to the largest = 0.50%
Alpha-2 removal
Alpha-1/alpha-2 ratio = 2.00
Calibration of 2-theta
SERIES # 1

| No | 2Theta | d | Rel I (%) | Max I | Integ I | Width | Type |
|---|---|---|---|---|---|---|---|
| Range # 1 | | | | | | | |
| 1 | 4.894 | 18.0405 | 8.0 | 69. | 227.78 | 0.164 | KA1 |
| 2 | 7.528 | 11.7334 | 100.0 | 866. | 3915.00 | 0.226 | KA1 |
| 3 | 9.805 | 9.0140 | 46.9 | 406. | 1807.78 | 0.222 | KA1 |
| 4 | 11.360 | 7.7830 | 63.8 | 553. | 2597.22 | 0.235 | KA1 |
| 5 | 12.816 | 6.9016 | 28.2 | 244. | 985.56 | 0.202 | KA1 |
| 6 | 14.730 | 6.0092 | 19.4 | 168. | 608.33 | 0.181 | KA1 |
| 7 | 15.662 | 5.6534 | 84.4 | 731. | 3580.56 | 0.245 | KA1 |
| 8 | 17.071 | 5.1900 | 9.0 | 78. | 253.89 | 0.162 | KA1 |
| 9 | 18.353 | 4.8301 | 16.5 | 143. | 502.22 | 0.176 | KA1 |
| 10 | 19.700 | 4.5029 | 45.8 | 396. | 2038.61 | 0.257 | KA1 |
| 11 | 20.500 | 4.3288 | 2.9 | 25. | 39.17 | 0.078 | KA1 |
| 12 | 20.745 | 4.2782 | 2.8 | 24. | 38.61 | 0.079 | KA1 |
| 13 | 20.957 | 4.2355 | 10.7 | 92. | 235.00 | 0.127 | KA1 |
| 14 | 21.407 | 4.1475 | 16.7 | 145. | 535.56 | 0.185 | KA1 |
| 15 | 22.110 | 4.0172 | 4.8 | 41. | 88.89 | 0.108 | KA1 |
| 16 | 22.834 | 3.8915 | 6.9 | 60. | 183.33 | 0.154 | KA1 |
| 17 | 23.062 | 3.8535 | 9.7 | 84. | 154.17 | 0.092 | KA1 |
| 18 | 23.950 | 3.7125 | 3.0 | 26. | 78.89 | 0.151 | KA1 |
| 19 | 24.245 | 3.6680 | 24.0 | 208. | 746.67 | 0.180 | KA1 |
| 20 | 24.682 | 3.6041 | 29.2 | 253. | 913.89 | 0.181 | KA1 |
| 21 | 25.055 | 3.5513 | 1.6 | 14. | 13.89 | 0.050 | KA1 |
| 22 | 25.341 | 3.5119 | 8.5 | 74. | 283.89 | 0.193 | KA1 |
| 23 | 26.244 | 3.3930 | 16.8 | 145. | 613.33 | 0.211 | KA1 |
| 24 | 27.296 | 3.2646 | 7.6 | 65. | 233.33 | 0.178 | KA1 |
| 25 | 28.801 | 3.0973 | 3.2 | 28. | 63.89 | 0.115 | KA1 |
| 26 | 29.351 | 3.0405 | 2.0 | 17. | 42.78 | 0.124 | KA1 |
| 27 | 33.687 | 2.6585 | 4.5 | 39. | 117.78 | 0.152 | KA1 |
| 28 | 34.292 | 2.6129 | 1.5 | 13. | 20.00 | 0.077 | KA1 |
| 29 | 34.814 | 2.5749 | 5.0 | 44. | 150.56 | 0.173 | KA1 |
| 30 | 35.305 | 2.5402 | 5.6 | 48. | 166.67 | 0.172 | KA1 |
| 31 | 36.894 | 2.4343 | 3.6 | 31. | 57.22 | 0.091 | KA1 |

USB29.RAW
CONT.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

All references cited in the present application are incorporated by reference in their entirety.

We claim:

1. Crystalline 2,4-diamino-5-methyl-6-[(3,4,5-trimethoxyanilino)methyl] quinazoline glucuronate.

2. Substantially pure crystalline 2,4-diamino-5-methyl-6-[(3,4,5-trimethoxyanilino)methyl] quinazoline glucuronate.

3. Anhydrous crystalline 2,4-diamino-5-methyl-6-[(3,4,5-trimethoxyanilino)methyl] quinazoline glucuronate.

4. A crystalline 2,4-diamino-5-methyl-6-[(3,4,5-trimethoxyanilino)methyl] quinazoline glucuronate solvate.

5. A pharmaceutical composition comprising crystalline 2,4-diamino-5-methyl-6-[(3,4,5-trimethoxyanilino)methyl] quinazoline glucuronate.

6. The pharmaceutical composition of claim 5 wherein the crystalline 2,4-diamino-5-methyl-6-[(3,4,5-trimethoxyanilino)methyl] quinazoline glucuronate is substantially pure.

7. The pharmaceutical composition of claim 5 wherein said pharmaceutical composition is suitable for parenteral administration.

8. The pharmaceutical composition of claim 5 wherein said pharmaceutical composition is suitable for oral administration.

9. The pharmaceutical composition of claim 5 wherein said pharmaceutical composition can be reconstituted to form a solution suitable for parenteral administration.

* * * * *